United States Patent [19]

Becker

[11] 4,254,063

[45] Mar. 3, 1981

[54] METHOD FOR PREPARING OLIGOMERIC ESTER CHAIN CONDENSATES OF SUBSTITUTED 1-HYDROXY-1,1-DIPHOSPHONIC ACID

[75] Inventor: Larry W. Becker, Wilmington, Del.

[73] Assignee: Betz Laboratories, Inc., Trevose, Pa.

[21] Appl. No.: 36,462

[22] Filed: May 7, 1979

[51] Int. Cl.$^3$ .............................................. C07F 9/40
[52] U.S. Cl. ................................... 260/931; 260/403; 260/968
[58] Field of Search ............... 260/931, 502.4 A, 403, 260/968

[56] References Cited

U.S. PATENT DOCUMENTS

| | | | |
|---|---|---|---|
| 3,149,151 | 9/1964 | Schiefer et al. | 260/502.4 A |
| 3,387,024 | 6/1968 | Quimby | 260/502.4 P |
| 3,400,151 | 9/1968 | Quimby et al. | 260/502.4 P |
| 3,496,222 | 2/1970 | Quimby et al. | 260/502.4 A |
| 3,562,169 | 2/1971 | Prentice | 260/931 X |
| 3,621,081 | 11/1971 | Prentice | 260/931 |
| 4,190,615 | 2/1980 | Becker | 260/931 |

*Primary Examiner*—Anton H. Sutto
*Attorney, Agent, or Firm*—Alexander D. Ricci

[57] ABSTRACT

A method is disclosed for preparing organo-phosphorous compounds which are oligomeric ester condensates of alkyl-1-hydroxy-1,1-diphosphonic acid.

17 Claims, No Drawings

METHOD FOR PREPARING OLIGOMERIC ESTER CHAIN CONDENSATES OF SUBSTITUTED 1-HYDROXY-1,1-DIPHOSPHONIC ACID

The present invention relates to a method for preparing organo-phosphorous compounds which are oligomeric ester condensates of alkyl-1-hydroxy-1,1-diphosphonic acid, most preferably those having as an end group a $C_6$–$C_{13}$ alkyl group.

BACKGROUND ART

Condensates of ethane-1-hydroxyl-1,1-diphosphonic acid are known such as those described in U.S. Pat. Nos. 3,387,024; 3,400,151 and 3,621,081. In the first two noted patents, the condensates are limited to dimers of ethane-1-hydroxy-1,1-diphosphonates joined by C-O-C bonds or P-O-P bonds, as opposed to the oligomeric ester compounds of the present invention which contain C-O-P bonds. While the latter mentioned patent U.S. Pat. No. 3,621,081 to Prentice does disclose oligomeric ester compounds of phosphorus acid which contain C-O-P bonds, the patent specifically limits the compounds to those containing a methyl end group. Not only were the preparatory methods of Prentice found to be unsuitable for preparation of the $C_6$–$C_{13}$ compounds of the present invention, but the higher homologs were unexpectedly found to possess "reverse" emulsion breaking properties not found in the Prentice oligomer.

DISCLOSURE OF THE INVENTION

The phosphonic acid ester condensate oligomers to which the present invention pertain have the general formula

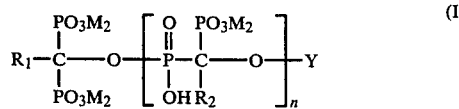

where $R_1$ and $R_2$ each represent a group but not necessarily the same group having the formula $C_xH_{2x+1}$, where x is from 6 up to and including 13; Y is

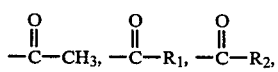

or hydrogen; M is a water soluble cation such as Na, K or $NH_4$; and where n is 1 or greater so long as the oligomer is water soluble. It is preferred that n have a value of from 1 to about 16. For $R_1$ and $R_2$ as defined above, x is preferably 7 up to 13 and, most preferably, from 7 to 11.

According to one aspect of the present invention, the oligomer is prepared by:

(1) Adding an excess amount of acetic anhydride to the appropriate substituted 1-hydroxy-1,1-diphosphonic acid, (2) continuing the reaction until it is substantially complete, and (3) separating the reaction product from the remaining reaction mixture.

As will become apparent from the examples below, this method of preparation is considered to be useful for preparing organo-phosphorous compounds in general which are oligomeric ester condensates of a substituted 1-hydroxy-1,1-diphosphonic acid and offers many advantages over the prior art method disclosed by Prentice.

The substituted 1-hydroxy-1,1-diphosphonic acid in preparation step (1) is represented by the general formula:

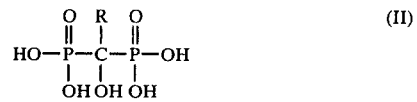

wherein R denotes an alkyl radical having 1 to 13, and preferably 3 to 13 (7 to 13 is most preferred), carbon atoms. These compounds and various methods for their preparation are well known in the art as evidenced by U.S. Pat. No. 3,214,454 to Blaser which is incorporated herein by reference. According to Blaser, these products can be produced, for example, by reacting phosphorous acid with acid chlorides or by reacting phosphorous trichloride with one of the carboxylic acids themselves. The reactions are opportunely carried out at elevated temperatures, preferably between 50° and 200° C.

Examples of compounds of Formula II are hydroxyheptane-, hydroxyoctane-, hydroxydecane-, and hydroxydodecane-1,1 diphosphonic acids.

With reference again to step (1) of the above-noted method for preparing the oligomer, it has been stated above that acetic anhydride is added to the "appropriate" substituted 1-hydroxy-1, 1-diphosphonic acid. The selection of the "appropriate" material is seen to be well within the skill of the art and would be achieved, for example, by properly matching the R group in Formula II with $R_1$ in Formula I. For example, if an oligomer of Formula I is to be made in which $R_1$ is heptyl, hydroxyoctane-1, 1-diphosphonic acid is used in step (1).

To assure that an excess of acetic anhydride is added to the substituted 1-hydroxy-1,1-diphosphonic acid, the mole ratio of acetic anhydride to the latter compound is preferably from about 2:1 to about 5:1.

The reaction temperature is in the range of about 50° to 200° C. If the production of the substituted 1-hydroxy-1,1-diphosphonic acid is included as part of the overall oligomerization process (as opposed to using the material already made), the compound will already be present at this elevated temperature which is required both to initiate the oligomerization and to increase the yield of oligomer by driving the reaction to completion. A preferred temperature range is about 100° to about 180° C.

Once the oligomerization reaction is initiated by adding the excess acetic anhydride to the substituted 1-hydroxy-1,1-diphosphonic acid, the reaction is continued until it is substantially complete. Depending on the particular alkyl radical present in the 1-hydroxy-1, 1-diphosphonic acid reactant, the final reaction product can take the form of a crunchy solid, an oily mass, or a solution. Of course, if an oily mass or crunchy solid is formed, the "substantial completion" of the reaction is readily detected. If after several hours of reaction time, no oily mass or solid is visible, it is to be assumed that the reaction product is in the form of a solution. The reaction could take as little as about 0.5 hour or as long as about 72 hours to go substantially to completion. However, about 1 to 4 hours is considered to be suitable time for the reaction to be continued.

In the instance that the reaction product takes the form of a crunchy solid, the solid can be directly separated from the remaining reaction mixture by any well known means, such as filtration.

In the event the reaction product takes the form of an oily mass, the mass should be cooled to about 0° to 25° C. If, as a result of cooling, a solid is formed, the product can be removed from the remaining reaction mixture by filtration. If the cooling step fails to provide a readily separable product, the product can be removed by evaporation of the remaining reaction mixture; or the supernatant can be decanted and replaced with fresh acetic anhydride. The decanting step is used to remove unreacted starting materials and acetic acid which was generated from the anhydride, since these materials tend to solubilize the reaction product. If, upon addition of the fresh acetic anhydride, a solid is formed, then separation of the product by filtration can be performed; whereas, if an oily mass persists, evaporation of the remaining reaction mixture must be resorted to.

If the reaction product takes the form of a solution, a recovery method similar to that for the oily mass is followed. First, the solution is cooled to about 0° to 25° C. If a solid is formed, then separation by filtration can be used; however, if an oily mass is formed either evaporation or the use of fresh acetic anhydride must be resorted to as discussed above.

According to the above-discussed Prentice patent, the oligomeric ester chain of ethane-1-hydroxy-1,1-diphosphonic acid (this would correspond to $R_1$ and $R_2 = CH_3$ in Formula I above) is prepared by reacting an excess of the appropriate anhydride, acetic anhydride, with phosphorous acid. According to that patent, the oligomeric ester chain condensate formed by the reaction is insoluble in the acetic anhydride and readily precipitates out of solution enhancing recovery of the product. When the present inventor attempted to utilize this method for preparing the oligomers of Formula I, where $R_1$ was greater than $C_2H_5$, by reacting phosphorous acid with the appropriate higher anhydrides, the Prentice method proved to be unsuitable for the purpose. It was observed that as the alkyl groups of the anhydride increased in the number of carbon atoms, the reaction products became more oil soluble and, therefore, soluble in the anhydride. As the product became soluble in the anhydride, it became extremely difficult to separate. In fact, as discussed in more detail below, the present inventor was unable to obtain any solid from the reaction mixture using the Prentice method. In contradistinction to the Prentice method, the present method permits easy recovery of the product. Another problem with the Prentice method is that as the alkyl groups of the anhydrides increase above $CH_3-$, they become either very expensive or commercially unavailable.

The oligomeric ester chain condensates of the present invention have been discovered to be useful as "reverse" emulsion breakers.

For example, in oil field applications, the major use of reverse emulsion breakers is at those areas where secondary oil recovery methods are being used. According to these methods, water, steam, air, fire, etc. are all used to liberate trapped oil from its geologic formation. The oil is then recovered as an oil-in-water emulsion. The recovered oil is then delivered to a physical separator or "knock-out". Free oil is removed from the separator and fed to other treatment areas. Without chemical treatment, a layer would remain in the separator as an emulsion. Chemical treatment causes the emulsion to become unstable and "break," that is separate into separate oil and water layers.

In secondary oil fields, the use of reverse emulsion breakers can also be found at those areas where slop oil is recovered and at water treatment facilities for further water cleanup prior to its reuse. Slop oils are those fractions which are inadvertently released from the wells, valves, pipes, etc., then collected and retained at a storage area for eventual oil recovery.

Of course, applications for reverse emulsion breakers are not limited to oil production fields. Other industrial applications would include, but are not necessarily limited to, oil removal at waste treatment facilities and from process waters and oil recovery in machining operations.

The preparation of oligomeric ester chain condensates according to the present invention is exemplified in Examples 1-4 below.

EXAMPLE 1

In this example the phosphorous acid ester condensate oligomer of 1-hydroxyheptane-1,1-diphosphonic acid was prepared as follows:

Heptanoic acid (97.6 g; 0.75 mole) and water (13.0 g; 0.75 mole) were mixed, followed by slow addition of phosphorous trichloride (68.5 g; 0.5 mole). Although initially exothermic, the reaction becomes endothermic with the evolution of HCl. As a result, the mixture was slowly heated to 145° C. where a thick one-phase system was formed. After one hour, 250 ml of acetic anhydride were added. A gummy solid formed within 15 minutes. After one hour, the mixture was cooled to 0° C., the mother liquor was decanted and replaced with a fresh aliquot of anhydride. After standing overnight, the mixture was again cooled to 0° C., excess anhydride was decanted and the residue was dried in vacuo to give 33.4 g of a tan product corresponding to formula I where $R_1$ and $R_2$ were $-C_6H_{13}$, and Y was H,

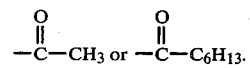

EXAMPLE 2

In this example the phosphorous acid ester condensate oligomer of 1-hydroxyoctane-1,1-diphosphonic acid was prepared as follows:

Octanoyl chloride (162 g; 1.0 mole) and phosphorous acid (82 g; 1.0 mole) were stirred and heated together to 145°-150° C. At this temperature, foaming was prevalent and boilover occurred. Accordingly, stirring was stopped to avoid boilover. The reaction mixture was then heated at 145° C. for 3 hours, cooled, and 250 cc of acetic anhydride were added. After about 1 hour the reaction mixture was cooled to 10° C., at which point a solid mass formed. The liquid was decanted and 200 ml of fresh acetic anhydride were added. The liquid was again decanted and the residue dried in vacuo to give 60 grams of product corresponding to Formula I where $R_1$ and $R_2$ were

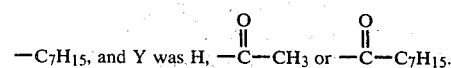

EXAMPLE 3

In this example the phosphorous acid ester condensate oligomer of 1-hydroxydecane-1,1-diphosphonic acid was prepared as follows:

Decanoyl chloride (60 g; 0.31 mole) and phosphorous acid (25.8 g; 0.31 mole) were heated with stirring to 150° C., where the two phases were miscible, and after a few minutes at 160° C., the mixture became thick, cloudy and exothermed to 180° C. Heating at 150° F. was then continued for 3 hours, at which point 200 ml of acetic anhydride were added. When the resulting reaction mixture was cooled an oily product appeared. An additional 100 ml of acetic anhydride was added causing a thick viscous oil to separate. The mixture was then cooled to 0° C., the liquid was decanted, and fresh acetic anhydride was added. After standing overnight the mixture was cooled to 10° C. and the liquid was again decanted. The residue was dried in vacuo to yield 32.8 g of product corresponding to Formula I where $R_1$ and $R_2$ were $-C_9H_{19}$ and Y was H,

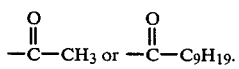

EXAMPLE 4

In this example the phosphorous acid ester condensate oligomer of 1-hydroxydodecane-1,1-diphosphonic acid was prepared as follows:

Lauroyl chloride (109.4 g; 0.5 mole) and phosphorous acid (41 g; 0.5 mole) were slowly heated with stirring to 170° C., at which point the mixture became thick with bubbling. After 15 minutes the bubbling stopped. Heating was continued at 160°–175° C. for 2 hours. The clear melt was poured into 200 ml of acetic anhydride and the temperature of the mixture was allowed to drop to room temperature. The mixture was then cooled to 10° C., but no separable product was formed. An additional 150 ml of acetic anhydride caused a precipitate to form. The liquid was decanted from the mixture and replaced with fresh acetic anhydride, and the mixture was allowed to warm to room temperature. After standing for 24 hours, a solid mass settled to the bottom of the flask. The liquid was then decanted and the mass was dried in vacuo to yield 68.4 grams of product corresponding to Formula I where $R_1$ and $R_2$ were $-C_{11}H_{23}$ and Y was

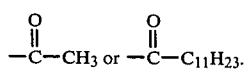

As already noted above, according to the Prentice patent the oligomeric ester chain of ethane-1-hydroxy-1,1-diphosphonic acid is prepared by reacting an excess of the appropriate anhydride, acetic anhydride, with phosphorous acid. It was also noted above that the Prentice method of preparation is unsuitable for the oligomers of the higher alkyl substituted materials because of extreme difficulty experienced in obtaining a separable product. This shortcoming of the Prentice method is demonstrated below in Examples 5–13.

EXAMPLE 5

In this example, phosphorous acid ester condensate oligomer was prepared from acetic anhydride, propionic anhydride and phosphorous acid according to the Prentice method as follows:

A mixture of 250 ml of acetic and 250 ml of propionic anhydride was prepared and heated to 55°–60° C. with 50 g (0.61 mole) of phosphorous acid until white crystals appeared, cooled to room temperature, and stirred for an additional 20 hours. The crystals were filtered, washed with ether and dried in vacuo to give 20 g of product corresponding to Formula I where $R_1$ and $R_2$ were $-CH_3/-C_2H_5$ or $-C_2H_5/-CH_3$ and Y was H,

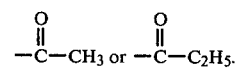

EXAMPLE 6

In this example, phosphorous acid ester condensate oligomer of 1-hydroxypropane-1,1-disphophonic acid was prepared from propionic anhydride according to the Prentice method as follows:

Propionic anhydride (250 ml) and 25 g (0.30 mole) of phosphorous acid were stirred and warmed to 55°–60° C. until a white solid formed (approximately 40 minutes), at which time the reaction mixture was cooled to room temperature. After stirring overnight, the product was a gummy mass, but after treatment with ether a white product was obtained which was dried in vacuo at 80° C. to give 23 g of product corresponding to Formula I where $R_1$ and $R_2$ were $-C_2H_5$ and Y was H, or

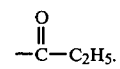

EXAMPLE 7

In this example, the preparation of phosphorous acid ester condensate oligomer of 1-hydroxybutane-1,1-diphosphonic acid from butyric anhydride according to the Prentice method was attempted as follows:

Butyric anhydride (500 ml) and 60 g of phosphorous acid were mixed and heated to 60° C. The mixture was kept at 60° C. for 2 hours with no solid being formed. The liquid mixture was stirred overnight at room temperature. Excess liquid was removed on a rotary evaporator at 80° C. and at 1–2 mm pressure. The thick oil which formed was treated extensively with ether, failing to yield any product.

EXAMPLE 8

While in Example 7 above the Prentice method proved unsuitable for preparing the oligomer of 1-hydroxybutane-1,1-diphosphonic acid from butyric anhydride and phosphorous acid, the successful preparation of the oligomer using a method according to the present invention was demonstrated as follows:

Butyryl chloride (53.3 g; 0.5 mole) and phosphorous acid (41 g; 0.5 mole) were slowly heated in a flask with magnetic stirring to 140° C., at which time the melt became very thick. After maintaining this temperature for 1 hour, the mixture was poured into 200 ml of acetic anhydride and warmed to 55°–60° C. for 15 minutes. Upon cooling and adding an additional 200 ml of acetic anhydride a white gummy material formed. Decanting the acetic anhydride and replacing it with fresh material produced a crunchy solid which was allowed to remain in contact with the anhydride for 24 hours. After filtering, washing with ether, and drying in vacuo, 29 g of solid were obtained which corresponded to Formula I where $R_1$ and $R_2$ were —$C_3H_7$ and Y was H,

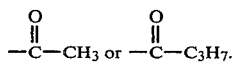

EXAMPLE 9

In this example, the preparation of phosphorous acid ester condensate oligomer of 1-hydroxyhexane-1,1-diphosphonic acid from caproic anhydride according to the Prentice method was attempted as follows:

Phosphorous acid (5.0 g) was heated to 60° C. with 50 ml of caproic anhydride, kept at that temperature for 30 minutes, and then cooled to room temperature. The mixture was then allowed to stir overnight. No solid was formed, even when the solution was cooled to 0°. Attempts to remove the excess anhydride and acid without darkening and decomposition using rotary evaporation failed.

EXAMPLE 10

While in Example 9 the Prentice method proved unsuitable for preparing the oligomer of 1-hydroxyhexane-1,1-diphosphonic acid, the successful preparation of the oligomer using a method according to the present invention was demonstrated as follows:

Hexanoyl chloride (63.0 g; 0.47 mole) and phosphorous acid (39.0 g; 0.47 mole) were slowly heated with magnetic stirring. At about 70° C. copious quantities of HCl were evolved and at 135°–140° C., the mixture became milky in color and finally at 140°–145° C., a one-phase melt was formed. The temperature rose to 170° C. with no adverse effects. After heating one hour at 150° C., the mixture was added to 250 ml of acetic anhydride. After 2 hours attempts to separate the product by cooling in an ice bath failed, therefore the excess acetic anhydride was removed on a rotary evaporator to give a dark oil which solidified when dried in vacuo. The dark brown solid product weighed 65 g and corresponded to Formula I where $R_1$ and $R_2$ where —$C_5H_{11}$ and Y was H,

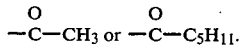

EXAMPLE 11

In Example 1 above an oligomer of 1-hydroxyheptane-1,1-diphosphonic acid was prepared using a method according to the present invention. For purposes of comparison, the preparation of the same oligomer was attempted using a method according to Prentice as follows:

Heptanoic anhydride (100 g; 0.41 mole) and phosphorous acid (8.2 g; 0.1 mole) were mixed and heated to 55°–60° C. The phosphorous acid remained unreacted at this temperature. Upon heating to 130° C., the phosphorous acid reacted to give a homogenous solution. Cooling the reaction mixture to ambient temperature gave no visible product after 2 days.

EXAMPLE 12

In this example, the use of a method according to the present invention for preparing the phosphorous acid ester condensate oligomer of 1-hydroxyethane-1,1-diphosphonic acid was demonstrated as follows:

Acetic acid (90.0 g; 1.5 mole) and water (27.0 g; 1.5 mole) were mixed and placed in a "Fleaker" equipped for magnetic stirring. An ice bath was added to cool the mixture while phosphorous trichloride (137.5 g; 1.0 mole) was slowly added. The first few grams caused considerable heat with copious quantities of HCl being evolved. After the water had apparently been consumed, the reaction mixture became endothermic and heating was necessary to maintain HCl evolution. The two layer mixture was heated to 125° C., where a one phase melt of phosphonic acid was formed. After 1 hour at this temperature, 250 ml of acetic anhydride were added all at once (exothermic with an immediate white solid). After two hours at room temperature, the mass was broken, washed with ether and dried in vacuo to give 70 g of product corresponding to Formula I where $R_1$ and $R_2$ were each —$CH_3$ and Y was H or

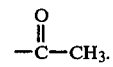

EXAMPLE 13

In Example 4 above an oligomer of 1-hydroxydodecane-1,1-diphosphonic acid was prepared using a method according to the present invention. For purposes of comparison, the preparation of the same oligomer was attempted using a method according to Prentice as follows:

Lauric anhydride (30.0 g; 0.09 mole) was warmed to a liquid with stirring. Phosphorous acid (3.0 g; 0.036 mole) was added to the melt, followed by slow heating to 180° C. The phosphorous acid never dissolved as with lower anhydrides. At 180°, decomposition of the anhydride was apparent, as a volatile liquid was evident, accompanied by darkening of the solution. After one hour at 150°–180°, the solution was cooled to ambient temperature where a solid mass of starting materials and possible products was formed. As a result, no oligomeric compounds could be isolated.

EXAMPLE 14

Several oligomeric materials corresponding to Formula I were tested for reverse emulsion breaking efficacy using oil samples from four different secondary oil production fields. The specific materials tested were those where $R_1$ and $R_2$ were —$CH_3$ (OP-1), —$C_3H_7$ (OP-3), —$C_7H_{15}$ (OP-7) and —$C_9H_{19}$ (OP-9); and 10% aqueous solutions were used.

The tests were conducted according to a testing procedure as follows:

1. the treatments were each added to a separate bottle using a microliter pipet;
2. the quantity added was such to correspond to 1, 5 and 10 ppm active material in 100 ml of solution;
3. a sample of untreated oil field emulsion was then added to each bottle;
4. each bottle was filled to 100 ml with emulsion;
5. each bottle was then capped and shaken vigorously by hand for a total of 100 shakes;
6. each bottle was then allowed to stand; and
7. visual observation was made of each solution, with any "break" of oil therefrom being noted.

The results of these tests are reported below in Table 1 wherein the different oil emulsion samples are simply labelled numerically as 1–4. In any instance in which a break was observed, this is indicated in the table as the dosage at which the break occurred.

TABLE I
TESTS FOR REVERSE EMULSION BREAKING EFFICACY

| Product | Oil Sample Number (1) | (2) | (3) | (4) |
|---|---|---|---|---|
| OP-1 | None | None | None | None |
| OP-3 | None | None | None | None |
| Op-7 | None | 10 ppm | 10 ppm | None |
| OP-9 | None | 10 ppm | 10 ppm | — |

As can be seen from the results in Table I, while the lower $C_1$ and $C_3$ homologs failed to demonstrate any such efficacy, the $C_7$ and $C_9$ materials demonstrated efficacy as reverse emulsion breakers.

While the lower and higher homologs of the subject oligomers did possess some properties in common, they were found to possess various mutually exclusive properties as demonstrated in the following examples. It should be kept in mind throughout the following examples that in the various OP designations followed by a number, the number refers to the number of carbon atoms in the $R_1$ and $R_2$ groups of Formula I.

Stability Toward Precipitation with Calcium

EXAMPLE 15

Tables II and III show the respective abilities of various oligomeric phosphonates to withstand various calcium concentrations at two temperatures. The test procedure used to determine calcium tolerance of the materials was as follows: Solutions containing 400 ppm $Ca^{+2}$ and 2000 ppm $Ca^{+2}$ were prepared at pH 9. To these, 20 ppm treatment was added and the pH was readjusted to 9 if necessary with NaOh. The solutions were placed in a water bath at 60° C. for 10 minutes. The presence of precipitation was detected by the Tyndall effect.

It is seen that for the oligomers where $R_1$ and $R_2$ were $C_1$ to $C_5$ alkyl groups, at 20 ppm calcium precipitate stability was demonstrated, even up to 1000 ppm calcium ion and at 60° C. However, for the higher homolog oligomers were $R_1$ and $R_2$ were $C_7$–$C_{11}$ precipitation occurred.

In summary, the results of Tables II and III demonstrate significant property differences between the lower and higher homologs with respect to stability toward precipitation with calcium.

TABLE II
STABILITY TOWARD PRECIPITATION WITH CALCIUM

| Treatment | T = 25° C. | T = 60° C. |
|---|---|---|
| OP-1 | clear | clear |
| OP-2 | clear | clear |
| OP-3 | clear | clear |
| OP-5 | clear | ppt |
| OP-7 | ppt | ppt |
| OP-9 | ppt | ppt |
| OP-11 | ppt | ppt |

Conditions:
20 ppm active treatment
400 ppm $Ca^{+2}$
pH = 9

TABLE III
STABILITY TOWARD PRECIPITATON WITH CALCIUM

| Treatment | T = 22° C. | T = 60° C. |
|---|---|---|
| OP-1 | clear | clear |
| OP-2 | clear | clear |
| OP-3 | clear | clear |
| OP-5 | clear | ppt |
| OP-7 | ppt | ppt |
| OP-9 | ppt | ppt |
| OP-11 | ppt | ppt |

Conditions:
20 ppm active treatment
1000 ppm $CA^{+2}$
pH = 9

Inhibition of Crystallization

EXAMPLE 16

Various oligomers were evaluated for their respective ability to prevent bulk phase precipitation of a salt at conditions for which the salt would usually precipitate.

In the results which follow several different salts commonly found in industrial water systems under various conditions were selected as precipitants. The results are expressed as "Percent Inhibition," with negative values implying that flocculation may have taken place, zero values implying that as much precipitate formed in the treated as in the non-treated systems, and positive values implying that the stated percentage of the precipitate was prevented from forming.

In Table IV are reported the results of tests conducted to determine the inhibition efficacy of the indicated oligomers with respect to calcium sulfate. The test procedure utilized to determine calcium sulfate inhibition was as follows: Solutions containing $3 \times 10^{-2}$ M $CaSO_4$ were prepared from $CaCl_2 \cdot 2H_2O$ and $Na_2SO_4$. The pH was adjusted to 4 and 11 for each series and 25 ml samples were added to test tubes. Treatments at the specified concentrations were added; the pH was readjusted if necessary; and the tubes were covered and placed in a water bath at 60° C. for a minimum of 14 hours. The solutions were cooled to room temperature and filtered through $0.2\mu$ filters. The soluble $Ca^{+2}$ was determined by titration with EDTA (ethylene diamine tetraacetic acid). The percent inhibition was calculated as follows:

$$\% \text{ Inhibition} = \frac{\text{ml titrant (treated)} - \text{ml titrant (control)}}{\text{ml titrant (maximum)} - \text{ml titrant (control)}} \times 100$$

The results for the inhibition of 4080 ppm calcium sulfate precipitation at pH 4 and 11 are given in Tables IV and V at treatment levels of 0.5, 1.0 and 3.0 ppm. At these levels of calcium sulfate and treatment the molar ratios of calcium to treatment (monomer molecular weight basis) are of the order of 700 to 1 up to 34,000 to 1. The following conclusions are inferred from these results:

a. At pH 4, the oligomeric phosphonates showed inhibition efficacy for only three members of the homologous series. The higher homologs demonstrated no significant efficacy.

b. At pH 11, similar to results at pH 4, there was a trend of decreased inhibition activity at a constant treatment level as the number of carbon atoms increased in the series. The lower homologs were considered to be far superior to the higher ones reported.

TABLE IV

CALCIUM SULFATE INHIBITION

| Treatment | Percent Inhibition | | |
|---|---|---|---|
| | 0.5 ppm | 1.0 ppm | 3.0 ppm |
| OP-1 | −1 | 2 | 71 |
| OP-2 | −3 | 0 | 33 |
| OP-3 | −1 | 0 | 48 |
| OP-7 | 0 | 0 | 10 |
| OP-9 | 0 | 0 | 4 |
| OP-11 | 0 | 0 | 2 |

Conditions:
4,080 ppm CaSO$_4$
60° C.
20 hours equilibration time
pH = 4

TABLE V

CALCIUM SULFATE INHIBITION

| Treatment | Percent Inhibition | | |
|---|---|---|---|
| | 0.5 ppm | 1.0 ppm | 3.0 ppm |
| OP-1 | 62 | 87 | 91 |
| OP-2 | 57 | 94 | 85 |
| OP-3 | 67 | 88 | 86 |
| OP-7 | 14 | 26 | 33 |
| OP-9 | 6 | 9 | 18 |
| OP-11 | 6 | 8 | 25 |

Conditions:
4,080 ppm CaSO$_4$
60° C.
20 hours equilibration time
pH = 11

EXAMPLE 17

In Table VI are reported the results of tests conducted to determine the inhibition efficacy of the indicated oligomers with respect to calcium carbonate. The test procedure utilized to determine calcium carbonate inhibition was as follows:

System:
  1,096 ppm Ca$^{++}$ as CaCO$_3$
  1,000 ppm CO$_3$= as CaCO$_3$
  pH=9
Chemicals per Liter:
  3.25 g CaCl$_2$·2H$_2$O (Solution 1)
  2.48 g Na$_2$CO$_3$·H$_2$O (Solution 2)
  1 N NaOH
  Calcium Indicator
  1 N HCl
Procedure:
  (1) 50 ml CaCl$_2$ preadjusted to pH 9
  (2) Treatment
  (3) 50 ml Na$_2$CO$_3$ preadjusted to pH 9
  (4) Heat 5 hours at 70° C. H$_2$O bath, cool to room temperature
  (5) Filter through 0.2μ filter (5 ml)
  (6) Adjust to pH<1.0 with HCl
  (7) Allow to stand overnight
  (8) Dilute to 50 ml with deionized water
  (9) Bring pH to 12.0 with NaOH
  (10) Add Ca$^{+2}$ indicator
  (11) Titrate with EDTA to purple-violet end point
Equipment:
  Brinkman PC 600 Colormeter
  Fisher Acumet 230 pH Meter
  Gelman filters in 6 head multi-filter
  Kimax 50 milliliter pipet
  Water bath capable of 100° C. range
  Kimex beakers (250 ml)
Calculation:

$$\% \text{ Inhibition} = \frac{\text{Soluble Ca}^{++} \text{ (treated)} - \text{Soluble Ca}^{++} \text{ (control)}}{\text{Soluble Ca}^{++} \text{ (theoretical maximum)} - \text{Soluble Ca}^{++} \text{ (control)}} \times 100$$

The results for the inhibition of 1,038 ppm calcium carbonate precipitation at pH 9 and at treatment levels of 5, 10 and 15 ppm are given in Table VI. From these results it was concluded that the lower homologs were more efficacious than the higher ones with respect to calcium carbonate inhibition.

TABLE VI

CALCIUM CARBONATE INHIBITION

| Treatment | Percent Inhibition | | |
|---|---|---|---|
| | 5 ppm | 10 ppm | 15 ppm |
| OP-1 | 55 | 28 | 53 |
| OP-2 | 63 | 69 | 89 |
| OP-3 | 54 | 47 | 48 |
| OP-7 | 31 | 18 | 33 |
| OP-9 | 22 | 23 | 23 |
| OP-11 | 4 | 8 | 28 |

Conditions:
1,038 ppm CaCO$_3$
70° C.
5 hours equilibration time
pH = 9

Having thus described my invention, I claim:

1. A method for preparing a compound having the formula

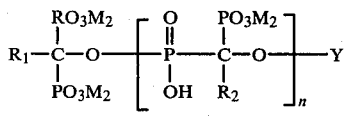

where M is a water soluble cation; R$_1$ and R$_2$ each represent a group having the formula C$_x$H$_{2x+1}$; x is from 1 to and including 13; Y is

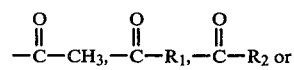

hydrogen, and n is 1 or greater so long as the compound is water soluble, which method comprises the steps of:
  (1) adding an excess amount of acetic anhydride to the appropriate substituted 1-hydroxy-1,1-diphosphonic acid,
  (2) continuing the reaction until it is at least substantially complete, and
  (3) separating the reaction product from the remaining reaction mixture.

2. A method according to claim 1, wherein n is from 1 to about 16 and wherein x is from 3 to and including 13.

3. A method according to claim 1, wherein the mole ratio of acetic anhydride to the 1-hydroxy-1,1-diphosphonic acid in step (1) is from about 2:1 to about 5:1.

4. A method according to claim 3, wherein the step (2) reaction time is about 0.5 to 72 hours.

5. A method according to claim 4, wherein said separating step comprises cooling the reaction mixture.

6. A method for the preparation of a compound having the formula

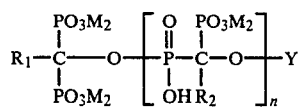

where M is a water soluble cation; $R_1$ and $R_2$ each represent a group having the formula $C_xH_{2x+1}$; x is from 6 to and including 13; Y is

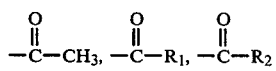

or hydrogen; and n is 1 or greater; which method comprises the steps of:
(1) adding an excess of acetic anhydride to the appropriate substituted 1-hydroxy-1,1-diphosphonic acid,
(2) continuing the reaction until it is at least substantially complete, and
(3) separating the reaction product from the remaining reaction mixture.

7. A method according to claim 6, wherein the mole ratio of acetic anhydride to 1-hydroxy-1,1-diphosphonic acid in step (1) is from about 2:1 to about 5:1, and wherein at the time the acetic anhydride is added in step (1) the 1-hydroxy-1,1-diphosphonic acid has a temperature of from about 50° to about 200° C.

8. A method according to claim 7, wherein the step (2) reaction time is from about 0.5 hours to about 72 hours.

9. A method according to claim 8, wherein said separating step comprises cooling the reaction mixture.

10. A method according to claim 9, wherein at the time the acetic anhydride is added in step (1) the 1-hydroxy-1,1-diphosphonic acid has a temperature of from about 100° to about 180° C., and wherein the reaction mixture is cooled in step (3) to from about 0° C. to about 25° C.

11. A method according to claim 10, wherein said separation step further comprises: after cooling said reaction mixture decanting the remaining acetic anhydride as supernatant and then adding an excess of fresh acetic anhydride.

12. A method according to claim 11, wherein the mole ratio of said fresh acetic anhydride to said precipitate is from about 2:1 to about 5:1.

13. A method according to claim 12, comprising the additional step of drying the product separated in step (3), wherein the product is separated in step (3) by filtration.

14. A method according to claim 10, wherein n is from about 1 to about 16, and wherein M is selected from the group consisting of hydrogen, sodium, potassium, ammonium, or ammonium salts.

15. A method according to claim 10, wherein the substituted 1-hydroxy-1,1-diphosphonic acid is made in step (1) prior to the addition of the acetic anhydride.

16. A method according to claim 15, wherein the substituted 1-hydroxy-1,1-diphosphonic acid is prepared by reacting the appropriate organic acid chloride and phosphorous acid.

17. A method according to claim 10, wherein the substituted 1-hydroxy-1,1-diphosphonic acid is prepared by reacting phosphorous trichloride and the appropriate carboxyic acid.

* * * * *